(12) United States Patent
Onik

(10) Patent No.: US 6,379,348 B1
(45) Date of Patent: Apr. 30, 2002

(54) COMBINED ELECTROSURGICAL-CRYOSURGICAL INSTRUMENT

(76) Inventor: Gary M. Onik, 8443 Foxworth Cir., Orlando, FL (US) 32819

(*) Notice: Subject to any disclaimer, the term of this patent is extended or adjusted under 35 U.S.C. 154(b) by 0 days.

(21) Appl. No.: 09/526,145

(22) Filed: Mar. 15, 2000

(51) Int. Cl.$^7$ .................................................. A61B 18/18
(52) U.S. Cl. ........................ 606/21; 606/22; 606/23; 606/41; 606/49
(58) Field of Search .................... 606/20–26, 41, 606/49

(56) References Cited

U.S. PATENT DOCUMENTS 5,423,807 A * 6/1995 Milder .......................... 606/20
5,733,280 A * 3/1998 Avitall .......................... 606/23
5,951,546 A * 9/1999 Lorentzen .................... 606/41

\* cited by examiner

*Primary Examiner*—Lee Cohen
(74) *Attorney, Agent, or Firm*—Lott & Friedland, P.A.

(57) ABSTRACT

The present invention is directed towards a combined electrosurgical-cryosurgical instrument for tissue ablation. The instrument comprises a shaft having a proximal end and a distal end, the distal end being electrically and thermally conductive; a radiofrequency insulation sheath surrounding the outer surface of the shaft; a cryo-insulation sheath surrounding a surface of the shaft; a radiofrequency power supply source; a cryogen supply tube within the shaft; and a cryogen supply source connected to the cryogen supply tube. The power source provides electrical energy to the distal end of the shaft, and the cryogen supply tube provides a cryogen to the distal end of the shaft.

17 Claims, 7 Drawing Sheets

COMBINED ELECTROSURGICAL-CRYOSURGICAL INSTRUMENT

TECHNICAL FIELD OF THE INVENTION

This invention relates to a combined electrosurgical-cryosurgical instrument for tissue ablation.

BACKGROUND OF THE INVENTION

Radiofrequency (RF) tissue ablation is a technique for making thermal lesions in tissue. The technique involves inserting a RF probe into tissue and then supplying the tip of the RF probe with RF energy. The tissue around the tip of the probe coagulates due to the heat produced surrounding the tip of the probe. The technique is commonly used to destroy tumors and other diseased tissue. The RF probe can be used superficially, surgically, endoscopically, laparascopically, or interstitially.

A RF lesion results from tissue destruction due to resistive heating that occurs in tissue surrounding the RF probe. Because resistive heating decreases rapidly as the distance from the RF probe increases, and because RF probes cause charring in the affected tissue, the size of lesions that have been obtained using conventional techniques have been limited. Typically, the maximum transverse diameter of RF lesions is about 10–15 mm. Organ L. W., Electrophysiologic Principles of Radiofrequency Lesion Making, Appl. Neurophysiol. 1976, 39:69–70.

Another technique for tissue ablation involves the use of a cryoprobe. Instead of heating tissue to cause it to coagulate, a cryoprobe destroys tissue by freezing it. One cryogenic tissue ablation technique involves inserting a cryoprobe into tissue and then providing a cryogen to the tip of the cryoprobe. As used herein, a cryogen is a substance such as, for example, a gas or a liquid, that provides a cryogenic effect. Typically, a high pressure cryogen gas is directed to the tip of the cryoprobe and then allowed to expand quickly, thereby producing a Joule-Thompson effect at the cryoprobe tip. Common cryogenic tissue ablation techniques involve the use of high pressure (e.g., about 80 psi) liquid nitrogen systems or high pressure (e.g., 2,800 psi) Joule-Thompson argon gas systems. In either method, the tissue surrounding the tip of the cryoprobe is frozen due to the cryogenic effect at the tip of the probe.

Thermal tissue ablation is replacing surgical tissue removal in many applications in the treatment of cancerous and benign conditions. Freezing (cryo-ablation) and heat (radiofrequency ablation) have been used successfully in various organs to destroy abnormal tissue. Radiofrequency ablation and cryo-ablation have different and potentially complimentary advantages. Cryo-ablation's advantages include the ability to create large lesions that are easily monitored using ultrasound and to have a beneficial immunologic effect. However, cryolesions often produce a toxic response in the patient when the lesions break down. This is because the cryo-ablation process does not denature the patient's tumor proteins. Radiofrequency lesions, on the other hand, have the advantage of being homeostatic while producing less systemic toxic effects because the ablated tissue is completely denatured. However, radiofrequency lesions usually cannot be made as large as cryolesions and are difficult to monitor using ultrasound.

U.S. Pat. No. 5,951,546 (Lorentzen) describes an electrosurgical instrument for tissue ablation. The instrument has a cooling supply that provides cooling fluid to the instrument during the tissue ablation process. The cooling fluid is used to cool the shaft of the instrument in order to prevent or reduce charring of tissue that is associated with radiofrequency lesion formation. The Lorentzen patent does not describe a combined electrosurgical-cryosurgical tissue ablation instrument. The entire contents of U.S. Pat. No. 5,951,546 are expressly incorporated by reference herein.

U.S. Pat. No. 5,906,612 (Chinn) describes a cryosurgical probe having insulating and heating sheaths. A thermally insulating sheath surrounds the cryosurgical probe. The size and shape of the ice ball produced by the probe can be controlled by varying the length and thickness of the thermally insulating sheath and the length of the distal tip of the probe. Alternatively, the size and shape of the ice ball can be controlled by surrounding the cryosurgical probe with a heated sheath having a heating element and a temperature sensor to detect the temperature to which the sheath is heated. The Chinn patent does not describe a combined electrosurgical-cryosurgical tissue ablation instrument. The entire contents of U.S. Pat. No. 5,906,612 are expressly incorporated by reference herein.

U.S. Pat. No. 4,202,336 (van Gerven) describes cauterizing probes for cryosurgery. The cryosurgical probe described in the van Gerven patent has a heating coil close to the freezing tip which operates through a highly heat conductive portion of the probe wall so as to cauterize previously frozen tissue. The disclosed heating coil does not produce a radiofrequency lesion. The van Gerven patent also describes a probe for cauterization only. That probe has the same heater, temperature sensor and insulating tip as the cryosurgical probe but it is equipped for circulating cooling water rather than cryogenic flow in the cooling space.

U.S. Pat. No. 5,807,395 (Mulier, et al.) describes a method and apparatus for radiofrequency ablation of tissue. In the disclosed method, radiofrequency ablation is accompanied by the infusion of a conductive solution into the tissue being treated so that a virtual electrode is created. The conductive fluid increases the conductivity of the tissue in the area being treated. As a result, the area of tissue being treated is enlarged as compared with non-fluid-assisted radiofrequency tissue ablation.

None of the aforementioned references describes or suggests a tissue ablation instrument that can be used to produce both a cryolesion and a radiofrequency lesion. Such an instrument would be highly desirable because it would permit medical personnel to make both types of lesions in a given area of tissue without having to remove the first tissue ablation instrument and insert a second tissue ablation instrument in the same place. In addition, such an instrument may provide the added benefit of facilitating creation of hybrid lesions which exhibit the advantageous characteristics of both cryolesion and radiofrequency lesions.

Consequently, there is a need in the art for a tissue ablation instrument that may be used to produce both a cryolesion and a radiofrequency lesion.

There is a further need in the art for a tissue ablation instrument that may be used to produce lesions that exhibit the advantageous characteristics of both cryolesions and radiofrequency lesions.

SUMMARY OF THE INVENTION

The present invention is directed towards a combined electrosurgical-cryosurgical instrument for tissue ablation comprising a shaft having a proximal end and a distal end, the distal end being electrically and thermally conductive; a radiofrequency insulation sheath surrounding the outer surface of the shaft, defining a radiofrequency-insulated portion of the shaft and a radiofrequency-noninsulated portion of the shaft; a cryo-insulation sheath surrounding a surface of the shaft, defining a cryo-insulated portion of the shaft and a cryo-noninsulated portion of the shaft; a radiofrequency power source connected to the shaft, wherein the power source provides electrical energy to the distal end of the shaft; a cryogen supply tube within the shaft, the cryogen supply tube extending from the proximal end of the shaft to the distal end of the shaft, wherein the cryogen supply tube has an open end portion at the distal end of the shaft; and a cryogen supply source connected to the proximal end of the cryogen supply tube.

In one embodiment, the instrument may be constructed such that the portion of the shaft that produces a radiofrequency lesion overlaps, partially or substantially entirely, with the portion of the shaft that produces a cryolesion. In this embodiment, the radiofrequency insulation sheath surrounds a portion of the outer surface of the shaft. The radiofrequency insulation sheath extends from the proximal end of the shaft to the distal end of the shaft, but leaves a portion of the distal end of the shaft uncovered. A cryo-insulation sheath surrounds a portion of the inner surface of the shaft. The cryo-insulation sheath extends from the proximal end of the shaft to the distal end of the shaft, but leaves a portion of the distal end of the shaft uncovered. Thus, a portion of the distal end of the shaft may be used to create a radiofrequency lesion, a cryolesion, and/or a lesion having characteristics of both a radiofrequency lesion and a cryolesion.

In another embodiment, the instrument may be constructed such that the portion of the shaft that produces a radiofrequency lesion is adjacent to a portion of the shaft that produces a lesion having characteristics of both a radiofrequency lesion and a cryolesion. In this embodiment the cryo-insulation sheath extends from the proximal end of the shaft to the distal end of the shaft, but leaves a portion of the distal end of the shaft uncovered. The radiofrequency insulation sheath surrounds a portion of the outer surface of the shaft. The radiofrequency insulation sheath extends from the proximal end of the shaft to the distal end of the shaft to a position that is proximal to the distal end of the cryo-insulation sheath.

In another embodiment, the instrument may be constructed such that the portion of the shaft that produces a radiofrequency lesion is adjacent to the portion of the shaft that produces a cryolesion. In this embodiment the radiofrequency insulation sheath surrounds a portion of the outer surface of the shaft. The radiofrequency insulation sheath extends from the proximal end of the shaft to the distal end of the shaft, but leaves a portion of the distal end of the shaft uncovered. A discontinuous cryo-insulation sheath surrounds the inner surface of the shaft. A first segment of cryo-insulation sheath extends from the proximal end of the shaft to the distal end of the shaft, but leaves a portion of the distal end of the shaft uncovered. The portion of the distal end of the shaft left cryo-noninsulated by the first segment of cryo-insulation sheath extends from a position proximal to the distal end of the radiofrequency insulation sheath to the distal tip of the shaft. A second segment of cryo-insulation sheath extends from the distal end of the radiofrequency insulation sheath to the distal tip of the shaft. In this embodiment, the instrument may be used to provide a radiofrequency lesion adjacent to a cryolesion. With respect to the instrument shaft, the radiofrequency lesion is provided distal to the cryolesion.

In another embodiment, the placement of the radiofrequency insulation sheath and cryo-insulation sheath may be reversed so that, with respect to the instrument shaft, the radiofrequency lesion is made adjacent to and proximal to the cryolesion. In this embodiment, the cryolesion insulation sheath surrounds the inner surface of the shaft and extends from the proximal end of the shaft to the distal end of the shaft, but leaves a portion of the distal end of the shaft cryo-noninsulated. A discontinuous radiofrequency insulation sheath surrounds the outer surface of the shaft. A first segment of radiofrequency insulation sheath extends from the proximal end of the shaft to the distal end of the shaft, but leaves a portion of the distal end of the shaft radiofrequency-noninsulated. The portion of the distal end of the shaft left radiofrequency-noninsulated by the first segment of radiofrequency insulation sheath extends from a position proximal to the distal end of the cryo-insulation sheath to the distal tip of the shaft. A second segment of radiofrequency insulation sheath extends from the distal end of the cryo-insulation sheath to the distal tip of the shaft. The radiofrequency lesion is thereby provided proximal to the cryolesion.

In all of the previously described embodiments, the cryo-insulation sheath may surround the outer surface of the shaft. The cryo-insulation sheath may lie between the radiofrequency insulation sheath and the outer surface of the shaft. Alternatively, the radiofrequency insulation sheath may lie between the cryo-insulation sheath and the outer surface of the shaft.

In another embodiment, the combined electrosurgical-cryosurgical instrument of the invention may have a single sheath that provides both radiofrequency insulation and cryo-insulation. In this embodiment, the radiofrequency insulation and cryo-insulation sheath surrounds a portion of the outer surface of the shaft. The portion of the shaft used to make a radiofrequency lesion is the same portion of the shaft that is used to make a cryolesion.

This invention also is directed towards a sheath for a tissue ablation instrument having an electrically insulating tubular surface and a radiofrequency power source connected to the electrically insulating tubular surface. The tubular surface has a first opening at a proximal end and a second opening at a distal end. When the sheath is placed over a surgical probe it surrounds the outer surface of the probe, and the radiofrequency power supply source makes electrical contact with the surgical probe. The sheath extends from the proximal end of the probe to the distal end of the probe while leaving a portion of the distal end of the probe radiofrequency-noninsulated. Consequently, the probe may be used to create a radiofrequency lesion in tissue. When the sheath is placed over a cryoprobe, a portion of the distal end of the probe may be used to create a radiofrequency lesion, a cryolesion, and/or a lesion having characteristics of both a radiofrequency lesion and a cryolesion.

It is an object of the present invention to provide a tissue ablation instrument that may be used to produce both a cryolesion and a radiofrequency lesion.

It is another object of the present invention to provide a tissue ablation instrument that may be used to produce lesions that exhibit the advantageous characteristics of both cryolesions and radiofrequency lesions.

Yet another object of the present invention is to provide a radiofrequency insulation sheath equipped with a radiofrequency power supply source, which radiofrequency sheath may be placed over a cryosurgical instrument to provide an instrument which may be used to produce both a cryolesion and a radiofrequency lesion.

These and other objects, features and advantages of the present invention may be more clearly understood and appreciated from a review of the following detailed description of the disclosed embodiments and by reference to the appended drawings and claims.

DETAILED DESCRIPTION OF THE INVENTION

Figure 1:
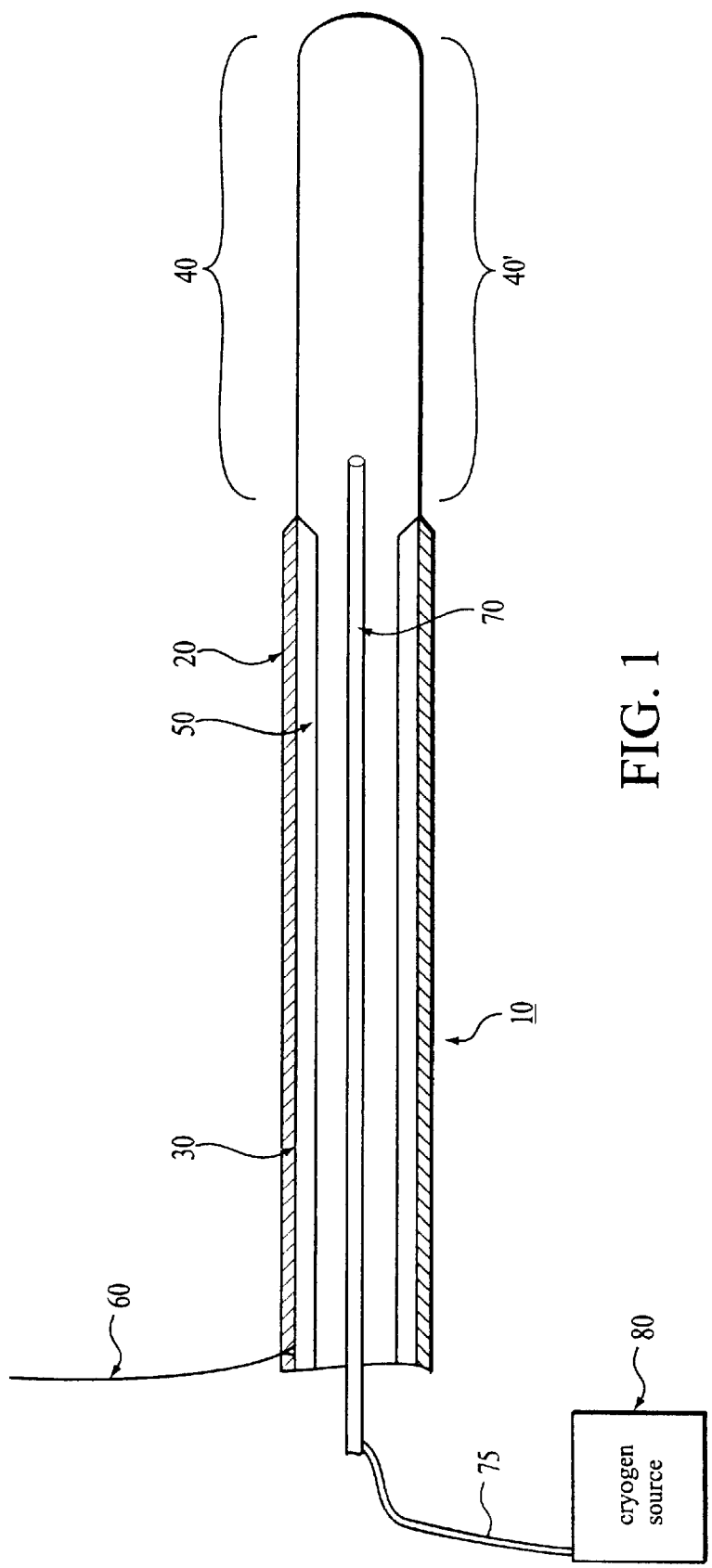
FIG. 1 is a cross-sectional view of a combined electrosurgical-cryosurgical instrument according to the invention in which the radiofrequency-noninsulated segment of the shaft overlaps substantially entirely with the cryo-noninsulated segment of the shaft.

Referring initially to FIG. 1 of the drawings, in which like numerals indicate like elements throughout the several views, in a preferred embodiment the combined electrosurgical-cryosurgical instrument is referred generally as 10. In FIG. 1 a first embodiment of combined electrosurgical-cryosurgical instrument 10 according to the invention is shown. Radiofrequency insulation sheath 20 surrounds the outer surface of shaft 30, and extends from a proximal end of shaft 30 to a distal end of shaft 30, leaving a segment 40 of the distal end of shaft 30 radiofrequency-noninsulated. Cryo-insulation sheath 50 surrounds the inner surface of shaft 30, and extends from a proximal end of shaft 30 to a distal end of shaft 30, leaving a segment 40' of the distal end of shaft 30 cryo-noninsulated. Radiofrequency power supply source 60 is in electrical contact with shaft 30, and provides electrical energy to segment 40 of shaft 30. Cryogen supply tube 70 within shaft 30, extends from the proximal end of shaft 30 to the distal end of shaft 30. Cryogen supply source 80 provides cryogen to the distal end of shaft 30 through cryogen supply tube 70. Cryogen connection tube 75 provides cryogen from cryogen supply source 80 to cryogen supply tube 70.

In operation, combined electrosurgical-cryosurgical instrument 10 may be inserted into tissue near the site to be ablated. Radiofrequency power supply source 60 may be used to deliver electrical energy to the distal end of shaft 30, and cryogen supply source 80 may be used to provide a cryogenic effect at the distal end of shaft 30. A radiofrequency lesion is formed in the tissue around the radiofrequency-noninsulated portion 40 of shaft 30. Similarly, a cryolesion is formed in the tissue around the cryo-noninsulated portion 40' of shaft 30.

Combined electrosurgical-cryosurgical instrument 10 also may be used to provide a hybrid lesion having characteristics of both a cryolesion and a radiofrequency lesion. This may be accomplished by supplying the distal end of the shaft with both radiofrequency energy and a cryogenic effect, either sequentially or simultaneously. The resultant hybrid lesion may possess the advantages of both radiofrequency lesions and cryolesion. For example, the hybrid lesion may be as large as a cryolesion, but not exhibit the toxicity effects that are associated with cryolesions upon breakdown. The hybrid lesion may exhibit the properties that would result from a cauterized cryolesion.

Figure 2:
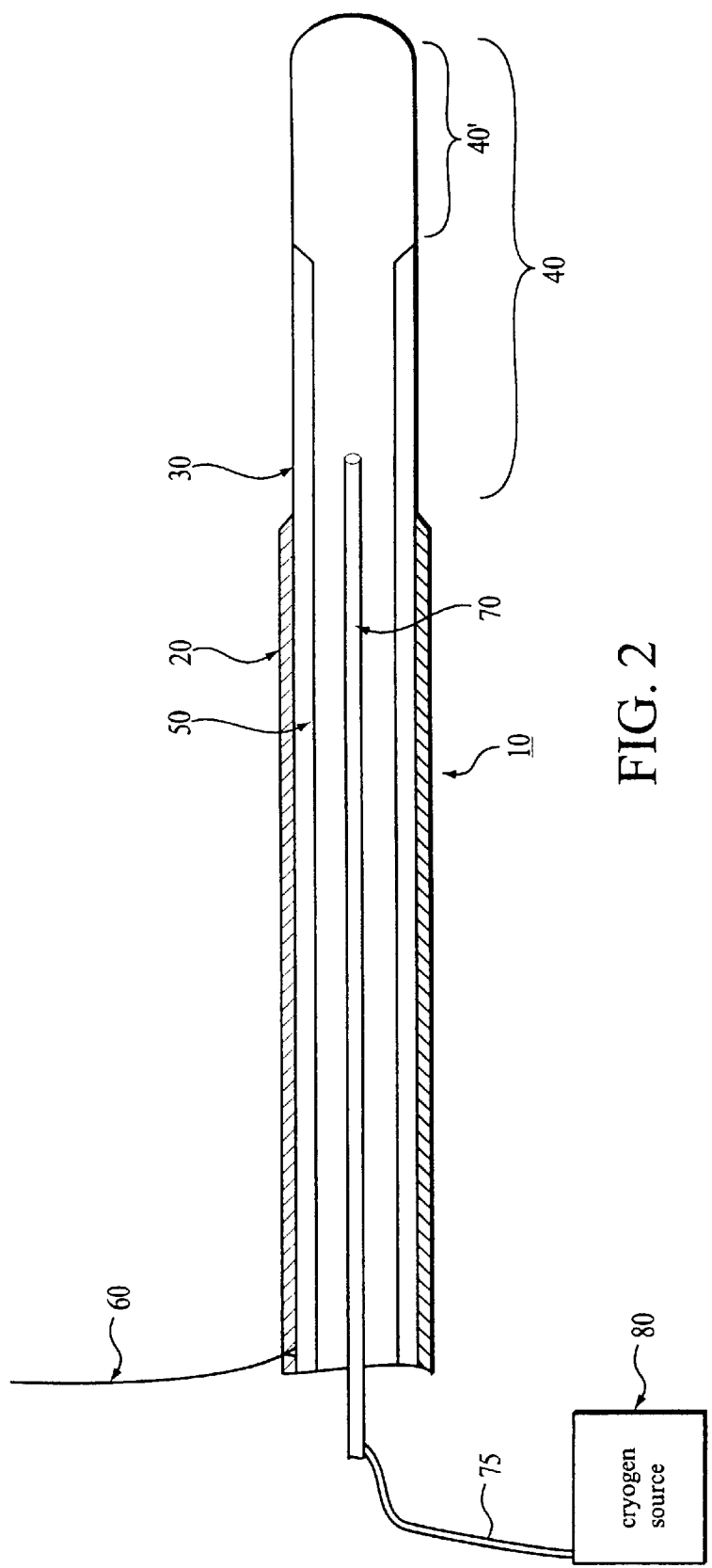
FIG. 2 is a cross-sectional view of a combined electrosurgical-cryosurgical instrument according to the invention in which the radiofrequency-noninsulated segment of the shaft overlaps partially with the cryo-noninsulated segment of the shaft.

In FIG. 2 a second embodiment of combined electrosurgical-cryosurgical instrument 10 according to the invention is shown. Cryo-insulation sheath 50 surrounds the inner surface of shaft 30, and extends from the proximal end of shaft 30 to the distal end of shaft 30, leaving a segment 40' of the distal end of shaft 30 cryo-noninsulated. Radiofrequency insulation sheath 20 surrounds the outer surface of shaft 30, and extends from a proximal end of shaft 30 to a distal end of shaft 30 to a position that is proximal to the distal end of cryo-insulation sheath 50. Consequently, radiofrequency noninsulated segment 40 partially overlaps with cryo-noninsulated segment 40'.

Radiofrequency power supply source 60 is in electrical contact with shaft 30, and provides electrical energy to segment 40 of shaft 30. Cryogen supply tube 70 within shaft 30, extends from the proximal end within shaft 30 to the distal end of shaft 30. Cryogen supply source 80 provides cryogen to the distal end of shaft 30 through cryogen supply tube 70. Cryogen connection tube 75 provides cryogen from cryogen supply source 80 to cryogen supply tube 70.

In operation, combined electrosurgical-cryosurgical instrument 10 may be inserted into tissue near the site to be ablated. The radiofrequency power supply source 60 may be used to deliver electrical energy to the distal end of the shaft 30, and cryogen supply source 80 may be used to deliver a cryogenic effect to the distal end of shaft 30. A radiofrequency lesion is formed in the tissue around the radiofrequency-noninsulated portion 40 of shaft 30. A cryo lesion is formed in tissue around the cryo-noninsulated portion 40' of shaft 30.

Combined electrosurgical-cryosurgical instrument 10 also may be used to provide a hybrid lesion having characteristics of both a cryolesion and a radiofrequency lesion. This may be accomplished by supplying the distal end of the shaft with both radiofrequency energy and a cryogenic effect, either sequentially or simultaneously.

Figure 3:
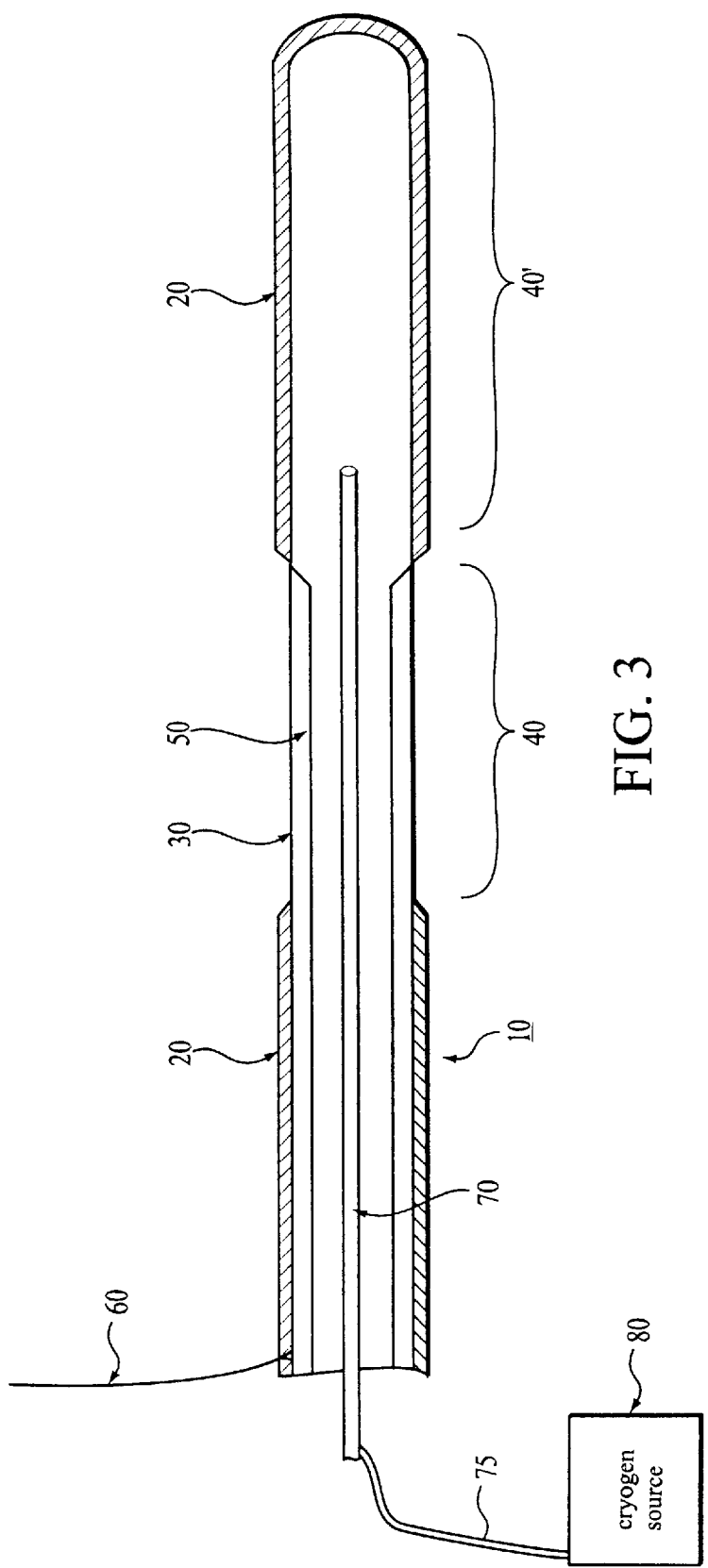
FIG. 3 is a cross-sectional view of a combined electrosurgical-cryosurgical instrument according to the invention in which the radiofrequency-noninsulated segment of the shaft lies adjacent to and proximal to the cryo-noninsulated segment of the shaft.

In FIG. 3 a third embodiment of combined electrosurgical-cryosurgical instrument 10 according to the invention is shown. Cryo-insulation sheath 50 surrounds the inner surface of shaft 30, and extends from the proximal end of shaft 30 to the distal end of shaft 30, leaving a segment 40' of the distal end of shaft 30 cryo-noninsulated. A first segment of radiofrequency insulation sheath 20 surrounds the outer surface of shaft 30, and extends from the proximal end of shaft 30 to the distal end of shaft 30, leaving a portion of the distal end of shaft 30 radiofrequency-noninsulated.

The portion of the distal end of the shaft 30 left radiofrequency-noninsulated by the first segment of radiofrequency insulation sheath 20 extends from a position proximal to the distal end of cryo-insulation sheath 50 to the distal tip of shaft 30. A second segment of radiofrequency insulation sheath 20 extends from the distal end of cryo-insulation sheath 50 to the distal tip of shaft 30. Together, the first and second segments of radiofrequency insulation sheath 20 define radiofrequency-noninsulated segment 40 of shaft 30.

Radiofrequency power source 60 is in electrical contact with shaft 30, and provides electrical energy to segment 40 of shaft 30. Cryogen supply tube 70 within shaft 30, extends from the proximal end within shaft 30 to the distal end of shaft 30. Cryogen supply source 80 provides cryogen to the distal end of shaft 30 through cryogen supply tube 70. Cryogen connection tube 75 provides cryogen from cryogen supply source 80 to cryogen supply tube 70.

In operation, combined electrosurgical-cryosurgical instrument 10 may be inserted into tissue near the site to be ablated. Radiofrequency power supply source 60 may be used to deliver electrical energy to the distal end of the shaft 30, and cryogen supply source 80 may be used to deliver a cryogenic effect to the distal end of shaft 30. A radiofrequency lesion is formed in the tissue around the radiofrequency-noninsulated portion 40 of shaft 30. A cryolesion is formed in the tissue around the cryo-noninsulated portion 40' of shaft 30. The radiofrequency lesion and the cryolesion may be formed either sequentially or simultaneously. With respect to shaft 30, the radiofrequency lesion is formed proximal to and adjacent to the cryolesion.

Figure 4:
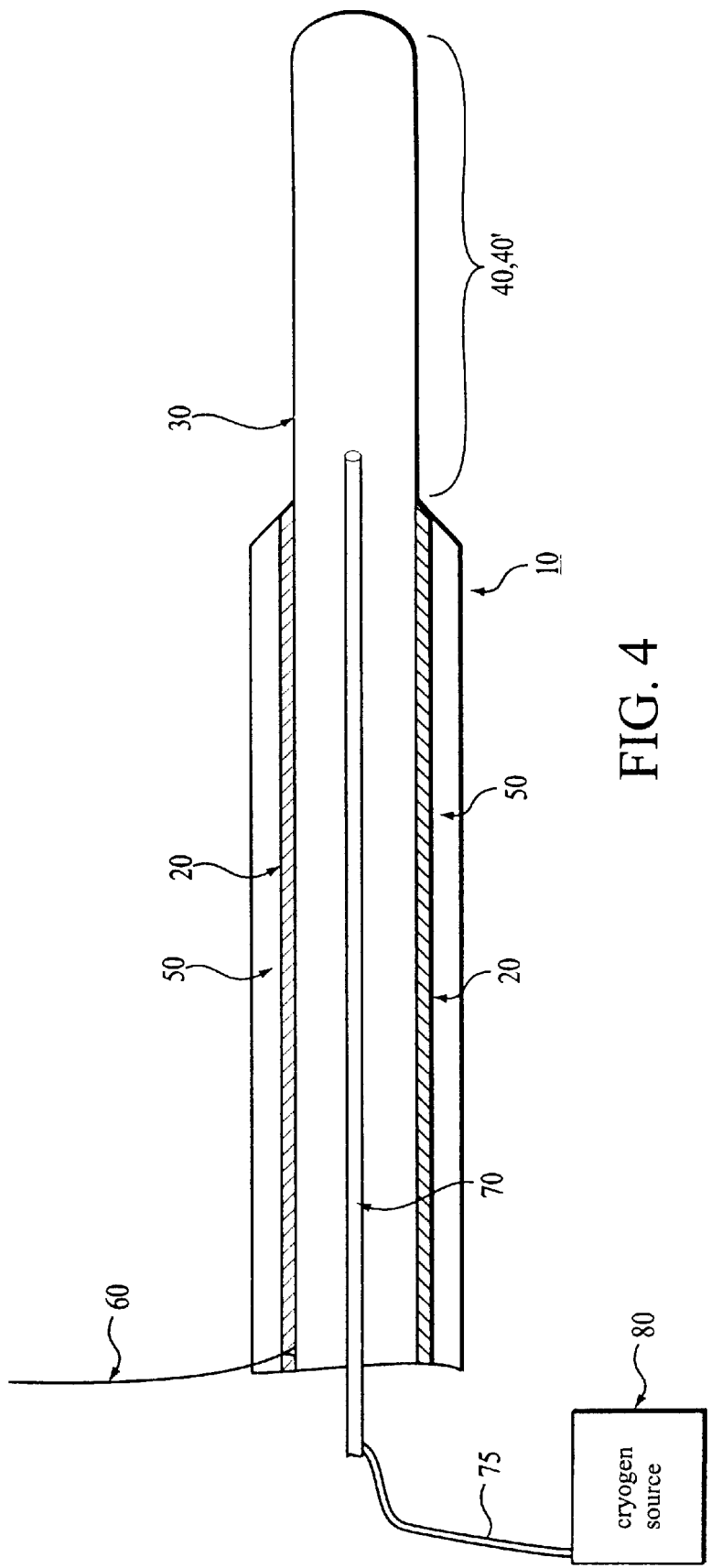
FIG. 4 is a cross-sectional view of a combined electrosurgical-cryosurgical instrument according to the invention in which the radiofrequency insulation lies between the cryo insulation and the outer surface of the shaft.

In FIG. 4 a fourth embodiment of combined electrosurgical-cryosurgical instrument 10 according to the invention is shown. Radiofrequency insulation sheath 20 surrounds the outer surface of shaft 30 and extends from a proximal end of shaft 30 to a distal end of shaft 30, leaving a segment 40 of the distal end of shaft 30 radiofrequency-noninsulated. In this embodiment, cryo-insulation sheath 50 surrounds the outer surface of shaft 30 and extends from a proximal end of shaft 30 to a distal end of shaft 30, leaving a segment 40' of the distal end of shaft 30 cryo-noninsulated. As shown in FIG. 4, radiofrequency insulation sheath 20 lies between the outer surface of shaft 30 and cryo-insulation sheath 50. Radiofrequency power supply source 60 is in electrical contact with shaft 30, and provides electrical energy to segment 40 of shaft 30. Cryogen supply tube 70 within shaft 30 extends from the proximal end within shaft 30 to the distal end of shaft 30. Cryogen supply source 80 provides cryogen to the distal end of shaft 30 through cryogen supply tube 70. Cryogen connection tube 75 provides cryogen from cryogen supply source 80 to cryogen supply tube 70. In this embodiment, radiofrequency-noninsulated segment 40 overlaps substantially entirely with cryo-noninsulated segment 40'.

In operation, combined electrosurgical-cryosurgical instrument 10 may be inserted into tissue near the site to be ablated. The radiofrequency power supply source may be used to deliver electrical energy to the distal end of shaft 30, and cryogen supply source 80 may be used to deliver a cryogenic effect to the distal end of shaft 30. A radiofrequency lesion is formed in the tissue around the radiofrequency-noninsulated segment 40 of shaft 30. Similarly, a cryolesion is formed in the tissue around the cryo-noninsulated segment 40' of shaft 30. Thus, a portion of the distal end of the shaft may be used to create a radiofrequency lesion, a cryolesion, or a lesion having characteristics of both a radiofrequency lesion and a cryolesion. The radiofrequency lesion and the cryolesion may be formed either sequentially or simultaneously.

Figure 5:
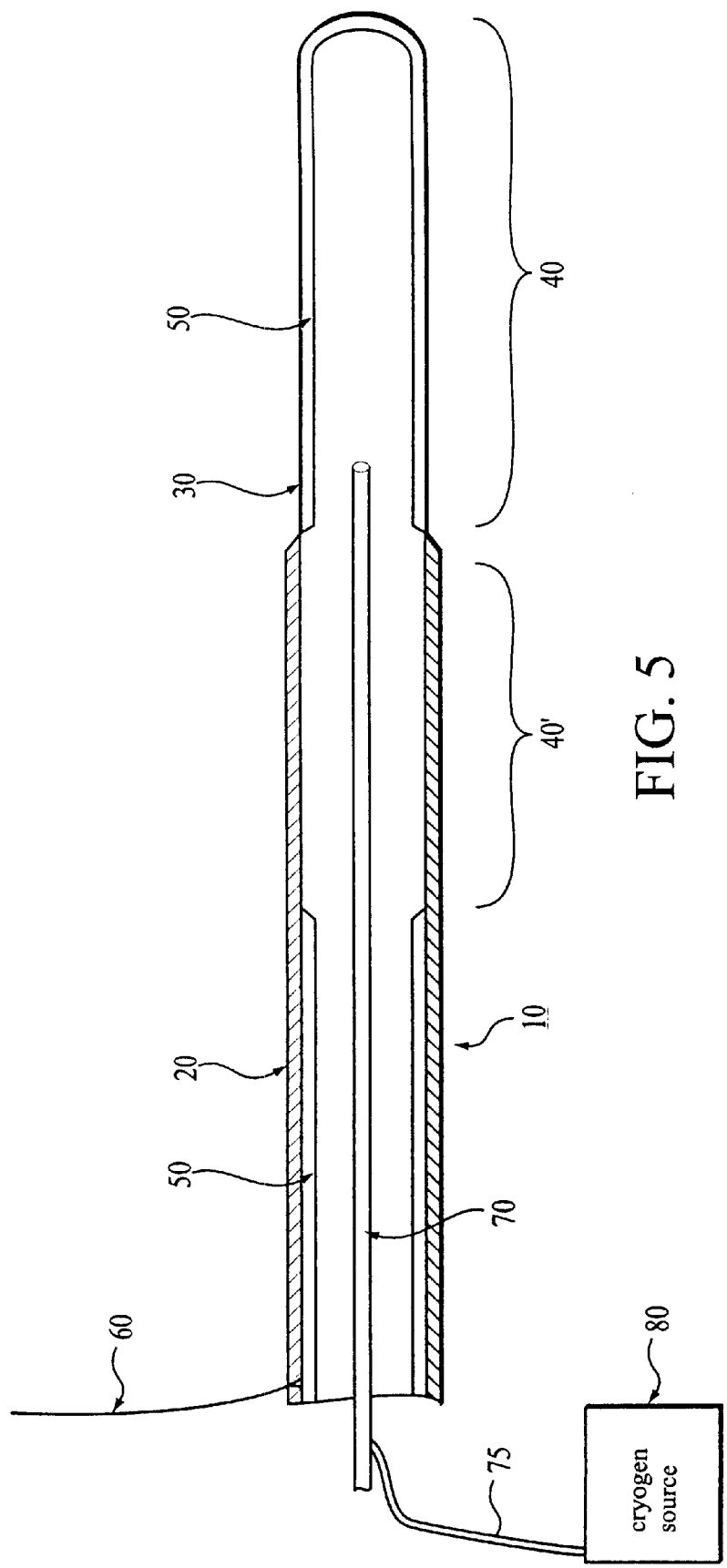
FIG. 5 is a cross-sectional view of a combined electrosurgical-cryosurgical instrument according to the invention in which the cryo-noninsulated segment of the shaft lies adjacent to and proximal to the radiofrequency-noninsulated segment of the shaft.

In FIG. 5 a fifth embodiment of combined electrosurgical-cryosurgical instrument 10 according to the invention is shown. Radiofrequency insulation sheath 20 surrounds the outer surface of shaft 30, and extends from the proximal end of shaft 30 to the distal end of shaft 30, leaving a segment 40 of the distal end of shaft 30 radiofrequency-noninsulated. A first segment of cryo-insulation sheath 50 surrounds the inner surface of shaft 30, and extends from the proximal end of shaft 30 to the distal end of shaft 30. The portion of the distal end of the shaft 30 left cryo-noninsulated by the first segment of cryo-insulation sheath 50 extends from a position proximal to the distal end of radiofrequency insulation sheath 20 to the distal tip of shaft 30. A second segment of cryo-insulation sheath 50 extends from the distal end of radiofrequency insulation sheath 20 to the distal tip of shaft 30. Together, the first and second segments of cryo-insulation sheath 50 define cryo-noninsulated segment 40' of shaft 30.

Radiofrequency power supply source 60 is in electrical contact with shaft 30, and provides electrical energy to segment 40 of shaft 30. Cryogen supply tube 70 within shaft 30, extends from the proximal end of shaft 30 to the distal end of shaft 30. Cryogen supply source 80 provides cryogen to the distal end of shaft 30 through cryogen supply tube 70.

In operation, combined electrosurgical-cryosurgical instrument 10 may be inserted into tissue near the site to be ablated. The radiofrequency power supply source 60 may be used to deliver electrical energy to the distal end of the shaft 30, and cryogen supply source 80 may be used to deliver a cryogenic effect to the distal end of shaft 30. A radiofrequency lesion is formed in the tissue around the radiofrequency-noninsulated portion 40 of shaft 30. A cryolesion is formed in the tissue around the cryo-noninsulated portion 40' of shaft 30. The radiofrequency lesion and the cryolesion may be formed either sequentially or simultaneously. With respect to shaft 30, the cryolesion is formed proximal to and adjacent to the radiofrequency lesion.

Figure 6:
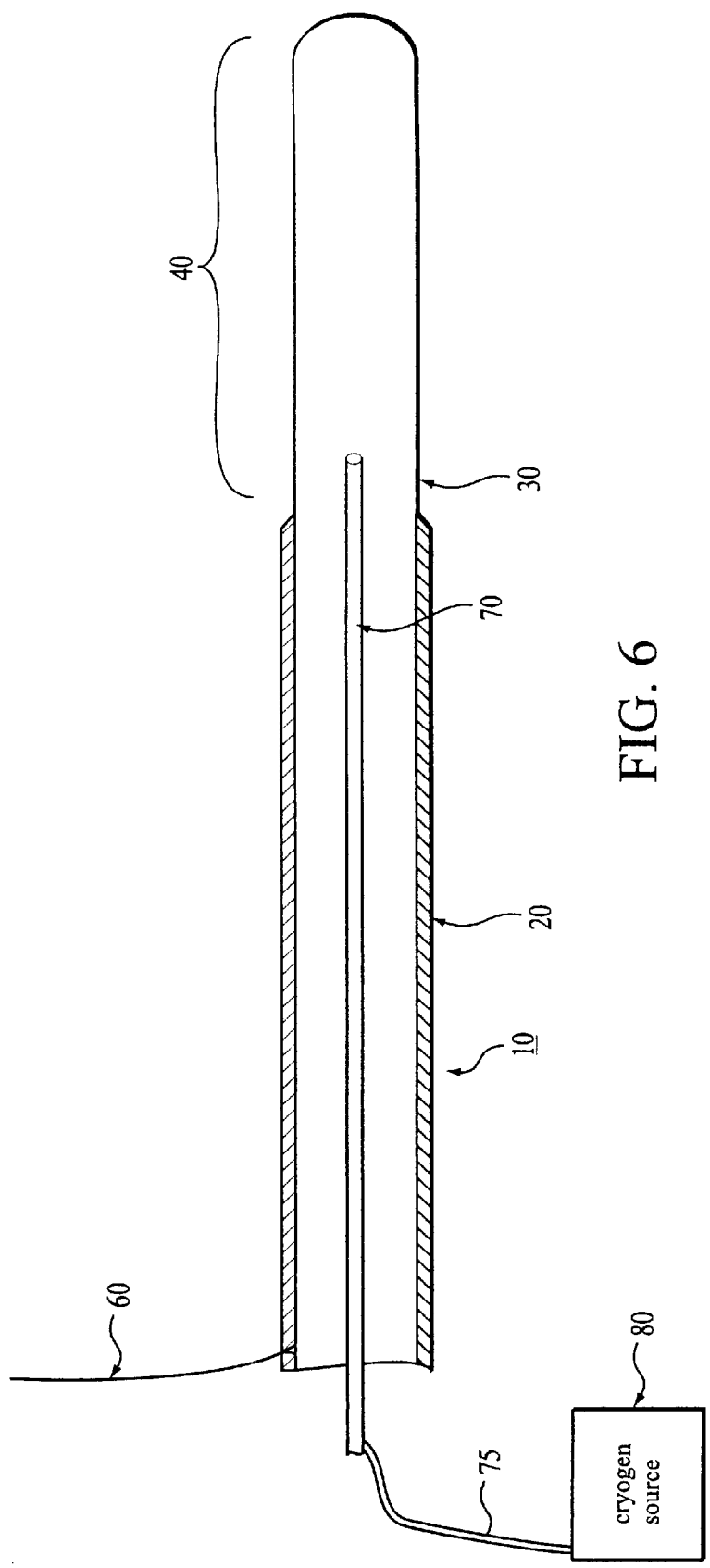
FIG. 6 is a cross-sectional view of a combined electrosurgical-cryosurgical instrument according to the invention in which a sheath surrounding the shaft provides both radiofrequency insulation and cryo insulation to the shaft.

In FIG. 6 a sixth embodiment of combined electrosurgical-cryosurgical instrument 10 according to the invention is shown. In this embodiment, the instrument has a single sheath 20 that provides both radiofrequency insulation and cryo-insulation. Sheath 20 surrounds the outer surface of shaft 30, and extends from the proximal end of shaft 30 to the distal end of shaft 30, leaving a segment 40 of the distal end of shaft 30 radiofrequency-noninsulated and cryo-noninsulated. Radiofrequency power source 60 is in electrical contact with shaft 30, and provides electrical energy to segment 40 of shaft 30. Cryogen supply tube 70 within shaft 30 extends from the proximal end within shaft 30 to the distal end of shaft 30. Cryogen supply source 80 provides cryogen to the distal end of shaft 30 through cryogen supply tube 70. Cryogen connection tube 75 provides cryogen from cryogen supply source 80 to cryogen supply tube 70.

In operation, combined electrosurgical-cryosurgical instrument 10 may be inserted into tissue near the site to be ablated. The radiofrequency power supply source may be used to deliver electrical energy to the distal end of the shaft 30, and cryogen supply source 80 may be used to deliver a cryogenic effect to the distal end of shaft 30. A radiofrequency lesion is formed in the tissue around the radiofrequency-noninsulated portion 40 of shaft 30. A cryolesion is formed in the tissue around the cryo-noninsulated portion 40' of shaft 30. The radiofrequency lesion and the cryolesion may be formed either sequentially or simultaneously.

Figure 7:
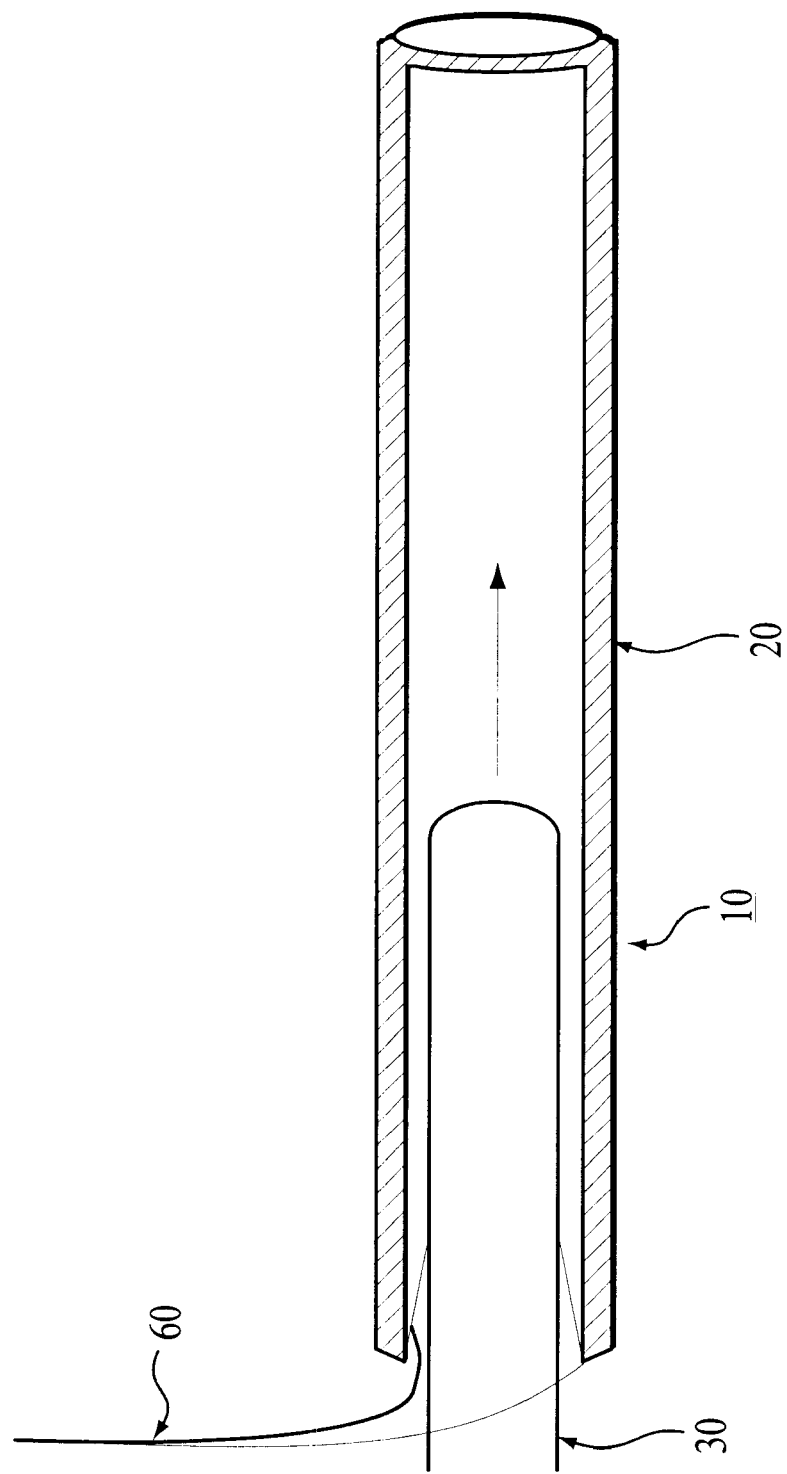
FIG. 7 is a cross-sectional view of a radiofrequency insulation sheath according to the invention. The sheath is electrically connected to a radiofrequency power supply source.

FIG. 7 shows a radiofrequency insulation sheath 20 for a tissue ablation instrument 10. Radiofrequency power source 60 is electrically connected to radiofrequency insulation sheath 20.

In operation, radiofrequency insulation sheath 20 is placed over tissue ablation instrument 10, leaving the distal tip of tissue ablation instrument 10 radiofrequency-noninsulated. When radiofrequency insulation sheath 20 is placed over tissue ablation instrument 10, radiofrequency power source 60 makes electrical contact with shaft 30 of tissue ablation instrument 10, and provides electrical energy to the radiofrequency noninsulated segment of shaft 30. Radiofrequency insulation sheath 20 may be placed over a cryosurgical instrument to provide a combined electrosurgical-cryosurgical instrument.

In each of the previously described embodiments, the shaft may be made of any material suitable for insertion into tissue, such as, for example, stainless steel. The radiofrequency insulation sheath may be made of any suitable material which prevents radiofrequency energy from passing between the shaft and the tissue being treated. For example, the radiofrequency insulation sheath may be made of Teflon®. Other suitable radiofrequency insulating materials include, without limitation, polypropylene and latex. The cryo-insulation sheath may be made of any suitable material which prevents a cryogenic effect from passing between the shaft and the tissue being treated. For example, the cryo-insulation sheath may be made of vacuum insulation. Other suitable cryo insulating materials include, without limitation, any closed cell foam such as Neoprene®.

Where the radiofrequency insulation sheath is also cryo insulating, it may be made of any suitable material which prevents radiofrequency energy and also a cryogenic effect from passing between the shaft and the tissue being treated. For example, such a sheath may be made of a closed cell foam.

The cryogen supply tube may be made of any suitable material for delivering cryogen to the distal end of the shaft. Typically, the cryogen supply tube is made of stainless steel, but any other suitable material may be used. For example, the cryogen supply tube also may be made of copper. The cryogen may be any substance that provides a cryogenic effect at the distal end of the shaft. Examples of such substances include, for example, liquid nitrogen and argon gas. A cryosurgical system based on liquid nitrogen is manufactured by Cryomedical Sciences, Inc. (Bethesda, Md.). A cryosurgical system based on argon gas is manufactured by EndoCare, Inc. (Irvine, Calif.).

The electric energy source of the instruments of the invention may be a constant power radiofrequency generator with a power output of 10–70 Watts and a frequency of 10 kHz to as high as 100,000 MHz. The power source may be timer controlled.

Radiofrequency lesions, cryolesions and lesions having characteristics of both a cryolesion and a radiofrequency lesion may be provided according to procedures well known by those skilled in the art.

Tissues that may be treated with the combined electrosurgical-cryosurgical instrument of the invention include mammal tissues, such as human tissues. Human tissues or tumor sites that may be treated with the electrosurgical instrument of this invention include, without limitation: bladder, brain, breast, cervix, colon, esophagus, kidney, gastric mass, large intestines, larynx, liver, lung, lymphoid, muscle, neck, oral cavity, ovaries, pancreas, pelvic region, prostate, small intestine, testis, and uterus.

The tissue ablation time may vary from about 20 seconds to about 20 minutes, or greater. Typically, the tissue is ablated from 5 to 15 minutes depending upon the size of the region to be ablated.

The shaft of the electrical instrument may be of any size suitable for providing the desired lesions in the target tissue. Typically, the shaft is from about 2 mm to about 5 cm long, and has a diameter from about 1 mm to about 8 mm.

The combined electrosurgical-cryosurgical instrument of the invention may be inserted into the tissue of a patient with the aid of a dilator. As those skilled in the art well know, a dilator is a rigid hollow tube that is commonly used to stretch the patient's tissue and create an access channel in the area of the tissue where the probe will be inserted. The dilator usually is made of plastic or stainless steel, and has a sharp point so that it can penetrate into the patient's tissue. The dilator may be inserted into the patient's tissue using methods well known to those skilled in the art (e.g., a Seldinger access technique). Typically, the dilator is surrounded by an insulation sheath. The insulation sheath may provide radiofrequency insulation, cryo insulation or both radiofrequency insulation and cryo insulation. The insulation sheath also may be connected to the radiofrequency power supply. Once the dilator forms the desired access channel to the target tissue, it is withdrawn, leaving behind the insulation sheath. The tissue ablation instrument (i.e., the combined electrosurgical-cryosurgical probe) may then be inserted into the access channel and through the insulation sheath. The insulation sheath surrounds the shaft of the probe, leaving a portion of the distal end of the probe noninsulated.

Accordingly, it will be understood that the preferred embodiments of the invention have been disclosed by way of example and that other modifications and alterations may occur to those skilled in the art without departing from the scope and spirit of the appended claims.

What is claimed is:

1. A combined electrosurgical-cryosurgical instrument for tissue ablation, comprising:
    a tubular shaft having an inner surface, a proximal end and a distal end with a distal tip at the farthest point of said instrument from said proximal end, said shaft being electrically and thermally conductive;
    a radiofrequency insulation sheath surrounding a portion of an outer surface of said shaft, said radiofrequency insulation sheath defining a radiofrequency-insulated segment of said shaft and a radiofrequency-noninsulated segment of said shaft;
    a cryo-insulation sheath surrounding a portion of a surface of said shaft, said cryo-insulation sheath defining a cryo-insulated segment of said shaft and a cryo-noninsulated segment of said shaft;
    a radiofrequency power source connected to said shaft, wherein said power source provides electrical energy to said distal end of said shaft;
    a cryogen supply tube within said shaft, said cryogen supply tube extending from said proximal end of said shaft to said distal end of said shaft; and
    a cryogen supply source connected to a proximal end of said cryogen supply tube.

2. The combined electrosurgical-cryosurgical instrument of claim 1, wherein said radiofrequency insulation sheath extends from said proximal end of said shaft to said distal end of said shaft.

3. The combined electrosurgical-cryosurgical instrument of claim 2, wherein said cryo-insulation sheath extends from said proximal end of said shaft to said distal end of said shaft.

4. The combined electrosurgical-cryosurgical instrument of claim 3, wherein said cryo-insulation sheath surrounds a portion of the inner surface of said shaft.

5. The combined electrosurgical-cryosurgical instrument of claim 4, wherein said radiofrequency-noninsulated segment of said shaft includes the distal tip of said shaft.

6. The combined electrosurgical-cryosurgical instrument of claim 4, wherein said cryo-noninsulated segment of said shaft includes the distal tip of said shaft.

7. The combined electrosurgical-cryosurgical instrument of claim 4, wherein said radiofrequency-noninsulated segment of said shaft overlaps with said cryo-noninsulated segment of said shaft.

8. The combined electrosurgical-cryosurgical instrument of claim 4, wherein said radiofrequency-noninsulated segment of said shaft is proximal to the distal tip of said shaft.

9. The combined electrosurgical-cryosurgical instrument of claim 8, wherein said radiofrequency-noninsulated segment of said shaft is adjacent to said cryo-noninsulated segment of said shaft.

10. The combined electrosurgical-cryosurgical instrument of claim 4, wherein said cryo-noninsulated segment of said shaft is proximal to the distal tip of said shaft.

11. The combined electrosurgical-cryosurgical instrument of claim 9, wherein said radiofrequency-noninsulated segment of said shaft adjacent to said cryo-noninsulated segment of said shaft.

12. The combined electrosurgical-cryosurgical instrument of claim 1, wherein said cryo-insulation sheath is disposed such that said cryogen supply tube provides a cryogenic effect at said distal end of said shaft.

13. The combined electrosurgical-cryosurgical instrument of claim 1, wherein said radiofrequency sheath is disposed such that said instrument produces a radiofrequency lesion in tissue around said distal end of said shaft.

14. The combined electrosurgical-cryosurgical instrument of claim 1, wherein said radiofrequency insulation sheath and cryo-insulation sheath are such that said shaft is radiofrequency-noninsulated, and cryo-noninsulated in portions, said instrument thereby producing a lesion having characteristics of both a cryolesion and a radiofrequency lesion.

15. A sheath for a tissue ablation instrument including an elongated surgical probe comprising an electrically insulating tubular surface and means for connecting to a radiofrequency power source connected to said electrically insulating tubular surface, said tubular surface having a first opening at a proximal end and a second opening at a distal end, wherein when said tubular surface is placed over said elongated surgical probe, said radiofrequency power source is in electrical contact with said elongated surgical probe.

16. A sheath according to claim 15, wherein said tissue ablation instrument is a cryoprobe.

17. A combined electrosurgical-cryosurgical instrument for tissue ablation, comprising:

a tubular shaft having a proximal end and a distal end, said shaft being electrically and thermally conductive;

a sheath surrounding a portion of an outer surface of said shaft, wherein said sheath is cryo-insulating and radiofrequency-insulating, said sheath defining a cryo-insulated and radiofrequency-insulated segment of said shaft and a cryo-noninsulated and radiofrequency-noninsulated segment of said shaft;

a radiofrequency power source connected to said shaft, wherein said power source provides electrical energy to said distal end of said shaft;

a cryogen supply tube within said shaft, said cryogen supply tube extending from said proximal end of said shaft to said distal end of said shaft, wherein said cryogen supply tube has an open end portion at said distal end of said shaft; and a cryogen supply source connected to said cryogen supply tube.

* * * * *